United States Patent
Wei et al.

(10) Patent No.: US 9,669,169 B2
(45) Date of Patent: Jun. 6, 2017

(54) SAFETY SYRINGE ASSEMBLY

(71) Applicants: Jun He Technology Co., Ltd., Changhua County (TW); Ching Hsiang Wei, Taichung (TW)

(72) Inventors: Ching Hsiang Wei, Taichung (TW); Chiang Ming Wang, Changhua County (TW); Hsing Jung Wei, Taichung (TW)

(73) Assignee: JUN HE TECHNOLOGY CO., LTD, Changhua County (TW)

( * ) Notice: Subject to any disclaimer, the term of this patent is extended or adjusted under 35 U.S.C. 154(b) by 187 days.

(21) Appl. No.: 14/744,037

(22) Filed: Jun. 19, 2015

(65) Prior Publication Data
US 2016/0367762 A1 Dec. 22, 2016

(51) Int. Cl.
*A61M 5/32* (2006.01)

(52) U.S. Cl.
CPC ... *A61M 5/3243* (2013.01); *A61M 2005/3247* (2013.01)

(58) Field of Classification Search
CPC .............. A61M 5/3245; A61M 5/3243; A61M 5/3246; A61M 5/3247; A61M 5/3271; A61M 5/3275; A61M 2005/3254
USPC ......................................... 604/198, 162, 263
See application file for complete search history.

(56) References Cited

U.S. PATENT DOCUMENTS 5,312,370 A * 5/1994 Talonn ................ A61M 5/3271
604/197
8,608,694 B2 12/2013 Lin

FOREIGN PATENT DOCUMENTS

TW           I255729  B      6/2006

* cited by examiner

*Primary Examiner* — Kevin C Sirmons
*Assistant Examiner* — Amber Stiles
(74) *Attorney, Agent, or Firm* — Pai Patent & Trademark Law Firm; Chao-Chang David Pai (57) ABSTRACT

A syringe assembly includes a syringe, a locking element and a protective sleeve. The syringe includes a needle connected to a cylinder. The protective sleeve is located on and around the cylinder and movable from a first position into a second position. The protective sleeve only covers the cylinder in the first position. The protective sleeve covers the needle in the second position. The locking element is adapted to keep the protective sleeve in the first position in a resilient manner. The locking element is further adapted to keep the protective sleeve in the second position. That is, after the protective sleeve is moved to the second position, return of the protective sleeve to the first position is prevented by the locking element.

8 Claims, 9 Drawing Sheets

SAFETY SYRINGE ASSEMBLY

BACKGROUND OF INVENTION

1. Field of Invention

The present invention relates to a syringe assembly and, more particularly, to a safety syringe assembly including a protective sleeve for completely covering a needle after use.

2. Related Prior Art

To protect a medical person from a needle, it is necessary to provide a protective mechanism for covering the needle after a syringe is used. As disclosed in U.S. Pat. No. 8,608,694, a typical protective mechanism includes a needle that can be completely retracted into a cylinder of a syringe. As disclosed in Taiwanese Patent No. I255729, a protective sleeve is movable along a cylinder of a syringe. After the use of the syringe, the protective sleeve is moved in a direction toward a needle of the syringe so that the protective sleeve completely covers the needle.

SUMMARY OF INVENTION

It is the primary objective of the present invention to provide a safety syringe assembly.

To achieve the foregoing objective, the safety syringe assembly includes a syringe, a locking element and a protective sleeve. The syringe includes a cylinder, a plunger and a needle. The plunger is movably inserted in the cylinder. The needle is connected to a front end of the cylinder. The locking element includes an annular body and two groups of teeth. The annular body is located on and around the front end of the cylinder. The first group of teeth is evenly formed on an external side of the annular body near a front end and separated by a first group of gaps. Each of the teeth in the first group includes a crown formed next to a slope. The second group of teeth is evenly formed on the external side of the annular body near a rear end and separated by a second group of gaps aligned to the first group of teeth. Each of the teeth in the second group is made with a thickness that gets smaller in a direction from a front end toward a rear end. The protective sleeve includes an annular rib and a frusta-conical face on an internal side. The annular rib is located near a rear end and includes a slope and a shoulder connected to a highest point of the slope. The frusta-conical face is located near a front end. The protective sleeve is movable along the cylinder between two positions. In the first position, the protective sleeve only covers the cylinder, and the slopes of the first group of teeth of the locking element abut against the frusto-conical face of the protective sleeve to keep the protective sleeve in the first position. In the second position, the protective sleeve completely covers the needle, the second group of the teeth of the locking element abuts against the shoulder of the annular rib of the protective sleeve, and the slopes of the first group of teeth of the locking element abut against the slope of the annular rib of the protective sleeve, thus keeping the protective sleeve in the second position.

In another aspect, the locking element further includes a third group of teeth evenly formed on an internal side near the second group of teeth. The third group of teeth is adapted for abutment against the front end of the cylinder to position the locking element on and around the front end of the cylinder.

Advantageously, the protective sleeve can be positioned on the cylinder and does not interfere with handling of the needle.

Advantageously, the protective sleeve can be pushed forwards on the cylinder to completely cover the needle to protect a medical person from the needle after use.

Advantageously, the protective sleeve involves a simple structure and is not too bulky to maneuver the syringe.

Advantageously, the locking element prevents the protective sleeve from moving backwards after the protective sleeve is moved forwards to completely cover the needle.

Advantageously, the locking element prevents the protective sleeve from moving further rearwards after the protective sleeve is moved forwards to completely cover the needle, thus keeping the protective sleeve on and around the cylinder.

Advantageously, the protective sleeve can easily be maneuvered by a single hand so that the medical person does not have to move his or her fingers near the needle.

Advantageously, during the movement of the protective sleeve on the cylinder to completely cover the needle, there is proper friction to enable the medical person to control the speed of the movement of the protective sleeve on the cylinder. Thus, safety is further improved.

Advantageously, the protective sleeve includes, at the front end, an annular flange for contact with the medical person's fingers to preventing the medical person's fingers from slipping on the protective sleeve.

Other objectives, advantages and features of the present invention will be apparent from the following description referring to the attached drawings.

BRIEF DESCRIPTION OF DRAWINGS

The present invention will be described via detailed illustration of the preferred embodiment referring to the drawings wherein.

DETAILED DESCRIPTION OF PREFERRED EMBODIMENT

Figure 1:
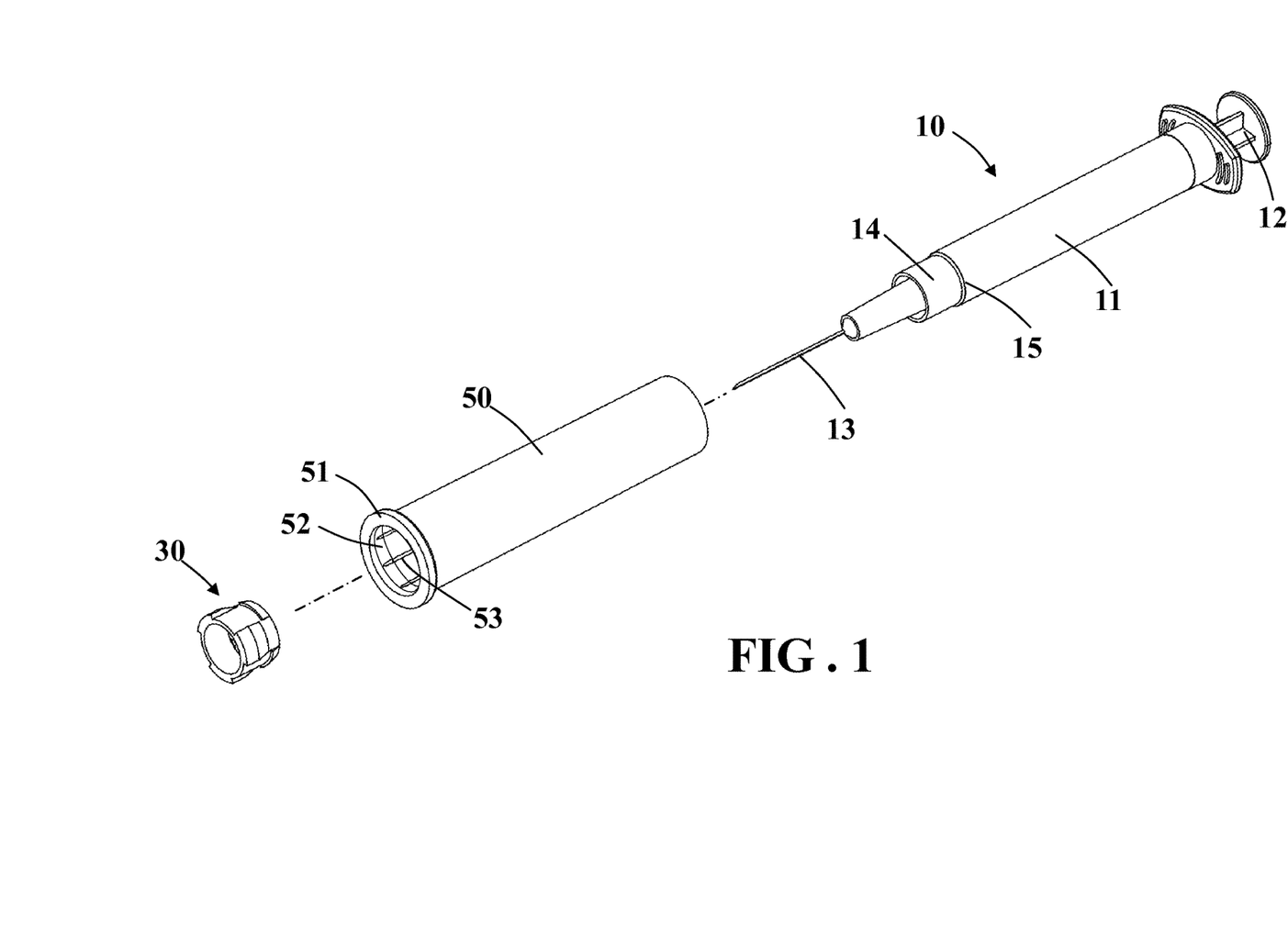
FIG. 1 is an exploded view of a syringe assembly according to the preferred embodiment of the present invention.
Figure 2:
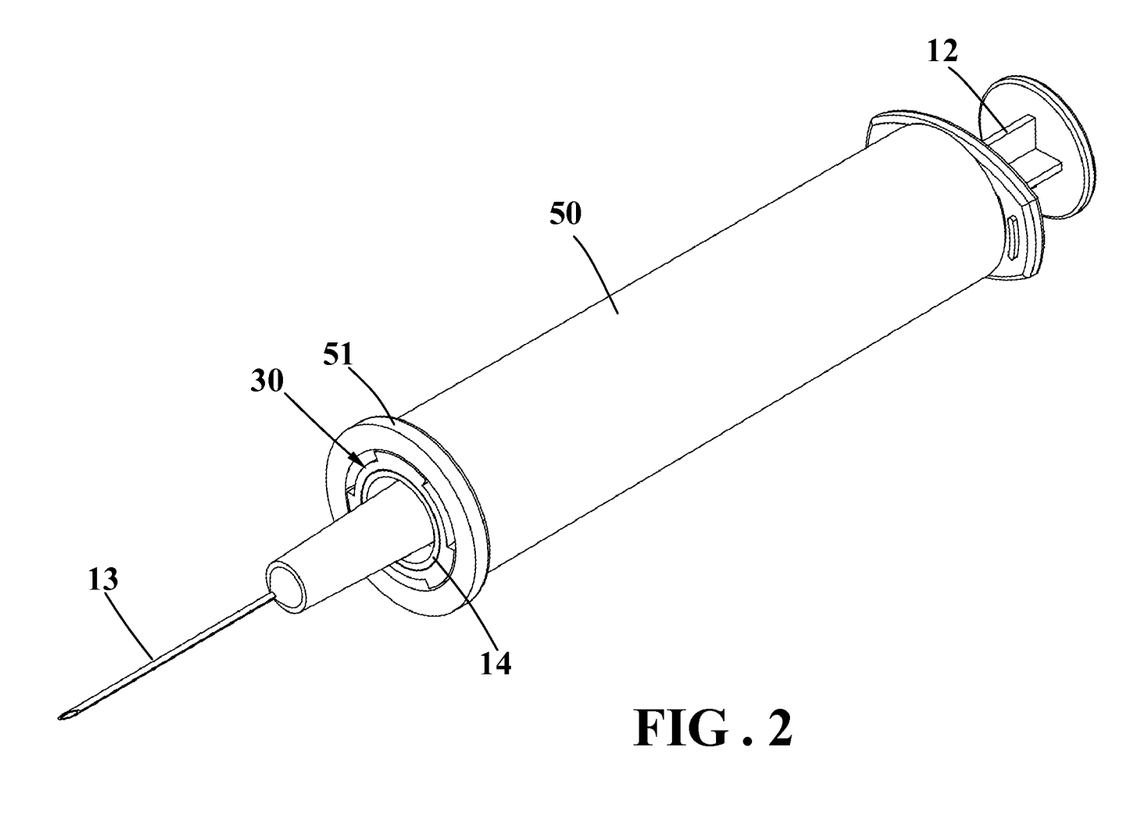
FIG. 2 is a perspective view of the syringe assembly illustrated in FIG. 1.
Figure 3:
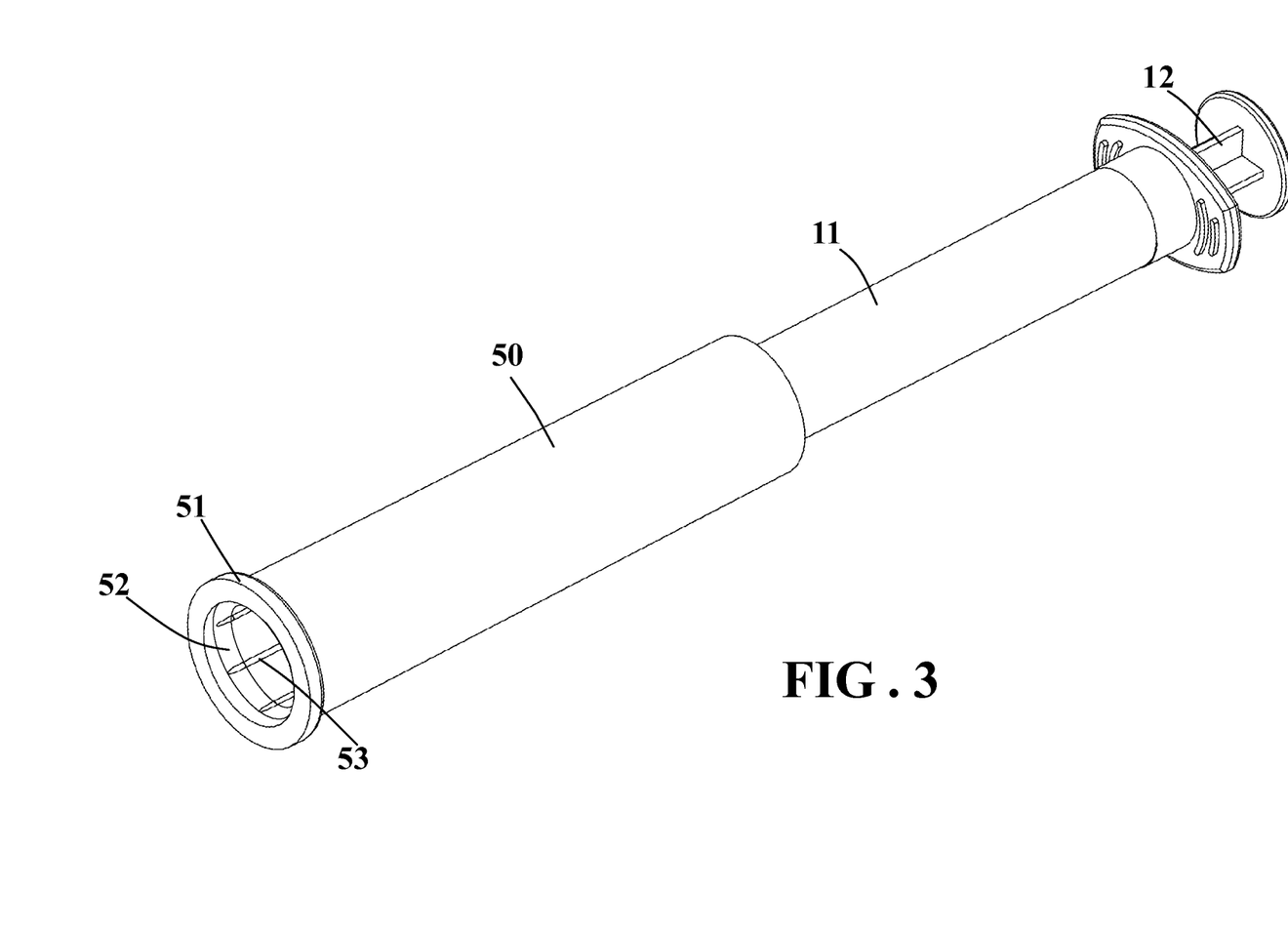
FIG. 3 is a perspective view of a syringe and a protective sleeve of the syringe assembly shown in FIG. 1.
Figure 4:
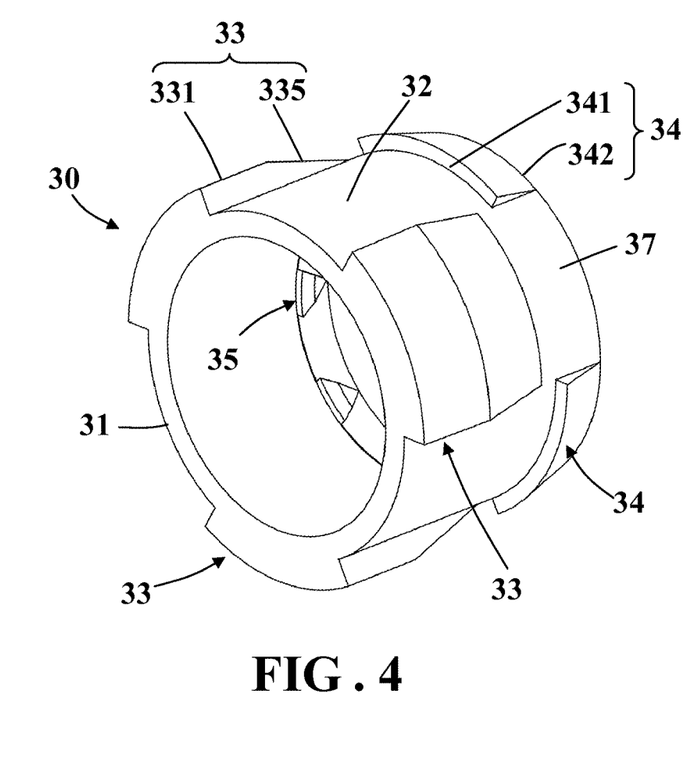
FIG. 4 is a perspective view of a locking element of the syringe assembly shown in FIG. 1.
Figure 5:
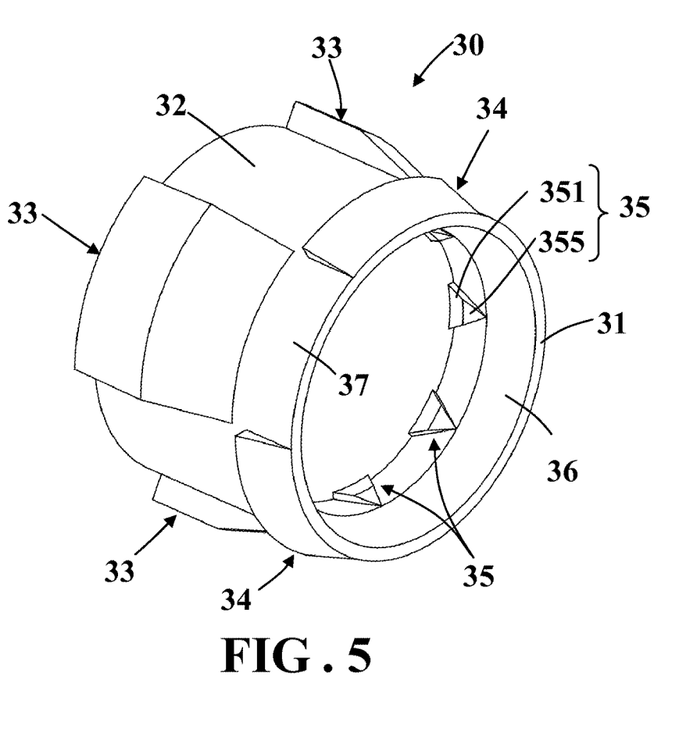
FIG. 5 is another perspective view of the locking element of the syringe assembly shown in FIG. 1.
Figure 6:
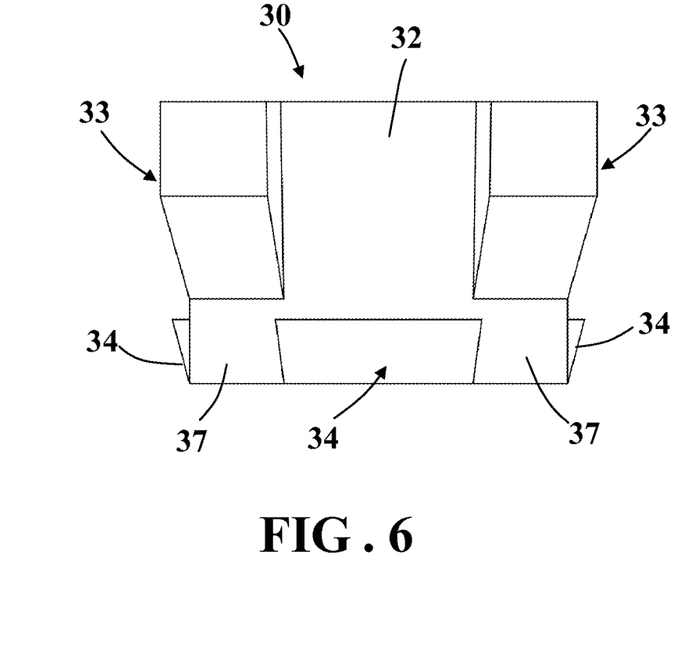
FIG. 6 is a side view of the locking element of the syringe assembly shown in FIGS. 4 and 5.
Figure 7:
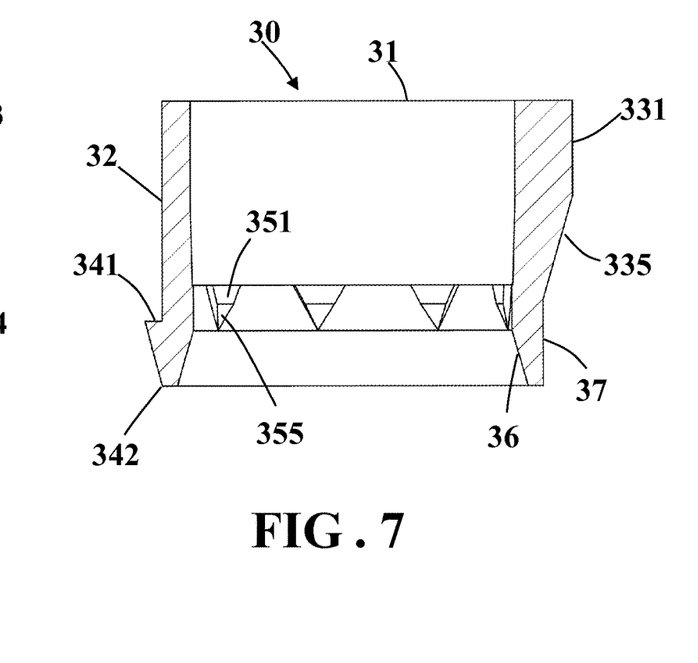
FIG. 7 is a cross-sectional view of the locking element of the syringe assembly shown in FIG. 6.

Referring to FIGS. 1 to 3, a syringe assembly includes a syringe 10, a locking element 30 and a protective sleeve 50 according to the preferred embodiment of the present invention. The syringe 10 includes a cylinder 11, a plunger 12 movably inserted in the cylinder 11, and a needle 13 connected to a front end 14 of the cylinder 11. The diameter of the front end 14 of the cylinder 11 is smaller than that of the other portion of the same. Thus, an annular shoulder 15 is formed next to the front end 14 of the cylinder 11.

The protective sleeve 50 includes two open ends. The protective sleeve 50 includes an annular flange 51 formed on an external side, near the front open end. The protective sleeve 50 includes a frusto-conical face 52 formed on an internal side, near the front open end. The frusto-conical face 52 gets larger toward the front open end. The protective sleeve 50 includes longitudinal ribs 53 evenly formed on the internal side. Each of the longitudinal ribs 53 includes a front end connected to the largest portion of the frusto-conical face 52 of the protective sleeve 50. The protective sleeve 50 is located on and around the cylinder 11.

The locking element 30 is located on and around the front end 14 of the cylinder 11. The locking element 30 keeps the protective sleeve 50 on the cylinder 11.

Referring to FIG. 2, the protective sleeve 50 is located on and around the cylinder 11 while the needle 13 is exposed.

The protective sleeve 50 can be moved on and along the cylinder 11 from the position shown in FIG. 2 to the position shown in FIG. 3, i.e., toward the needle 13. Thus, the protective sleeve 50 completely covers the needle 13.

Referring to FIGS. 4 to 7, the locking element 30 includes an annular body 31, a first group of teeth 33, a second group of teeth 34, and a third group of teeth 35. The first group of the teeth 33 is evenly located on a front portion of an external side of the annular body 31. The first group of teeth 33 is separated by a first group of gaps 32. Each of the teeth 33 includes a crown 331 and a slope 335. The slope 335 includes a highest point connected to the crown 331. The slope 335 includes a lowest point connected to the external side of the annular body 31.

The second group of teeth 34 is evenly located on a rear portion of the external side of the annular body 31. The second group of teeth 34 is separated by a second group of gaps 37. The second group of teeth 34 is aligned to the first group of gaps 32. The second group of gaps 37 is aligned, to the first group of teeth 33. Each of the teeth 34 is made with a thickness that gets smaller in a direction from a first end 341 toward a second end 342. The first end 341 of each of the teeth 34 is located next to a corresponding one of the gaps 32.

The third group of teeth 35 is evenly located on a rear portion of an internal side of the annular body 31. The third group of teeth 35 is separated by a third group of gaps (not numbered). Each of the teeth 35 includes a crown 351 and a slope 355. The slope 355 includes a highest point connected to the crown 351. The slope 355 includes a lowest point connected to the internal side of the annular body 31 and a smallest portion of the frusto-conical face 36 of the annular body 31.

Figure 8:
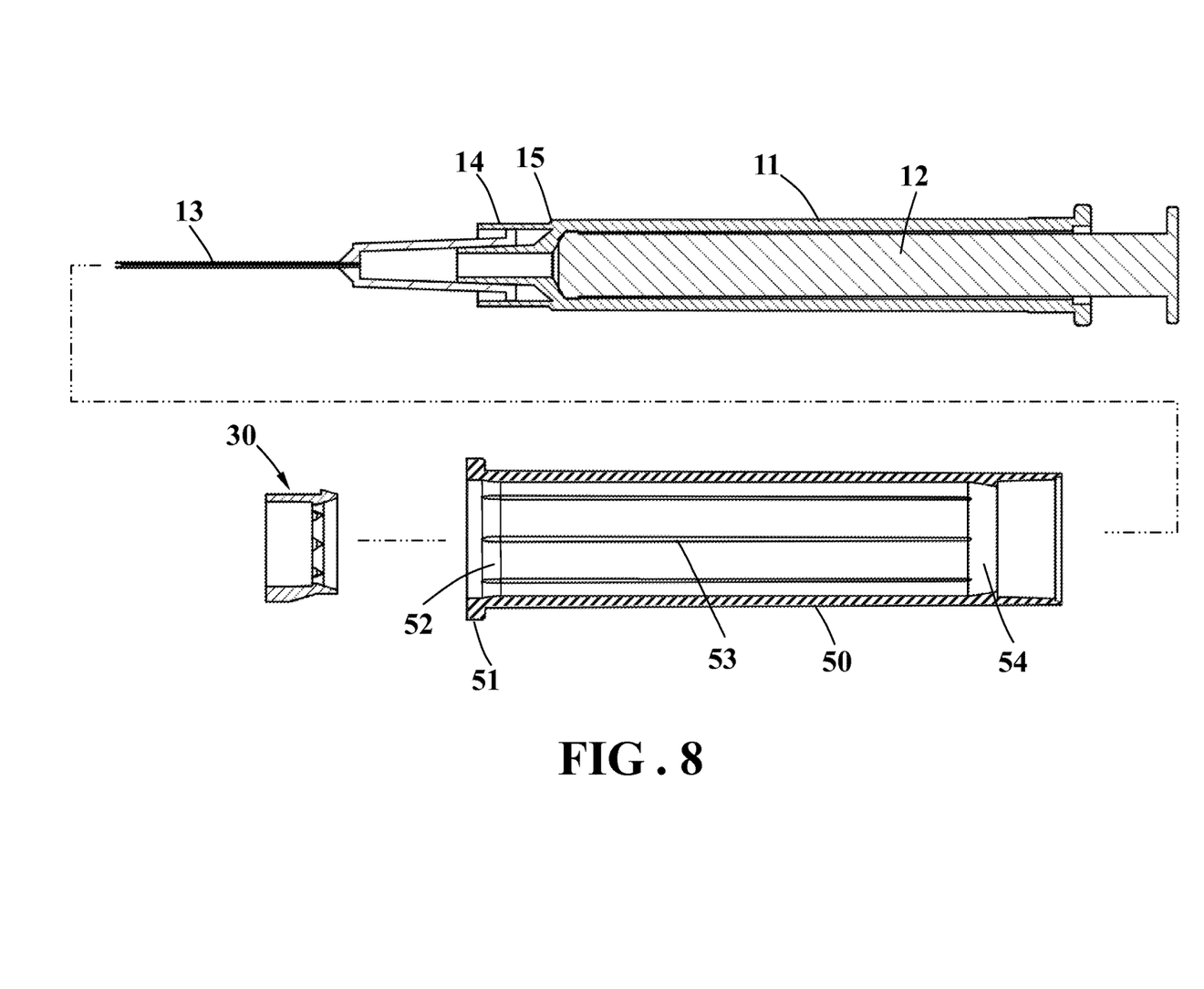
FIG. 8 is a cross-sectional view of the syringe assembly shown in FIG. 2.
Figure 9:
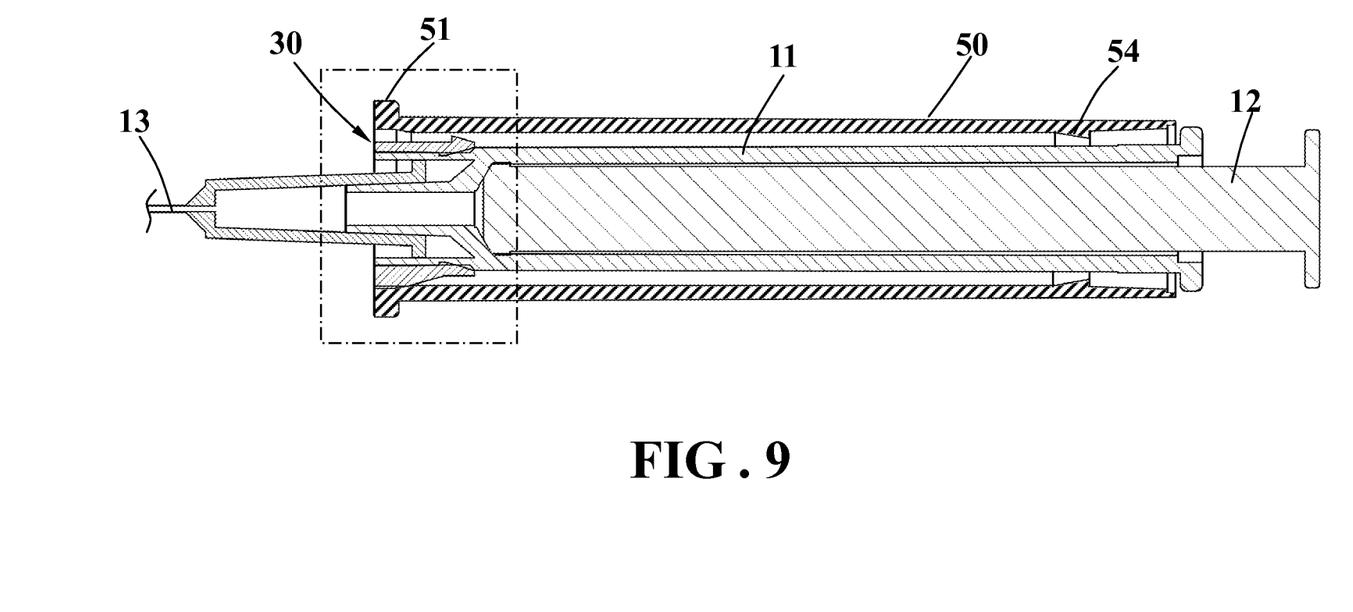
FIG. 9 is a cross-sectional view of the syringe assembly in another position than shown in FIG. 8.
Figure 11:
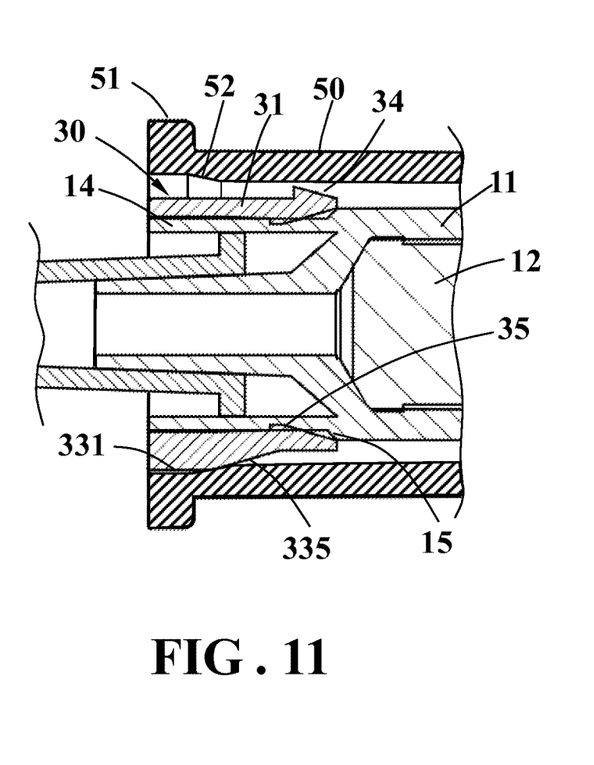
FIG. 11 is an enlarged partial view of the syringe assembly shown in FIG. 9.

Referring to FIGS. 8, 9 and 11, the protective sleeve 50 is located on and around the cylinder 11. The locking element 30 is located on and around the front and 14 of the cylinder 11. The locking element 30 is smoothly moved past the front end 14 of the cylinder 11 because of the frusto-conical face 36 and the slopes 355 of the third group of teeth 35 before the locking element 30 is stopped by the annular shoulder 15 of the cylinder 11.

The locking element 30 is made of a plastic material that is harder than a plastic material used to make the front end 14 of the cylinder 11. Hence, the crowns 351 of the third group of teeth 35 tightly press and bite at the front end 14 to position the locking element 30 relative to the front end 14 of the cylinder 11 when the locking element 30 is located on and around the front end 14 of the cylinder 11.

The slopes 335 of the first group of teeth 33 of the locking element 30 stop the frusto-conical face 52 of the protective sleeve 50 and the front ends of the longitudinal ribs 53. Therefore, the locking element 30 stops the protective sleeve 50 and keeps the protective sleeve 50 in position on the cylinder 11 without a considerable force.

Figure 10:
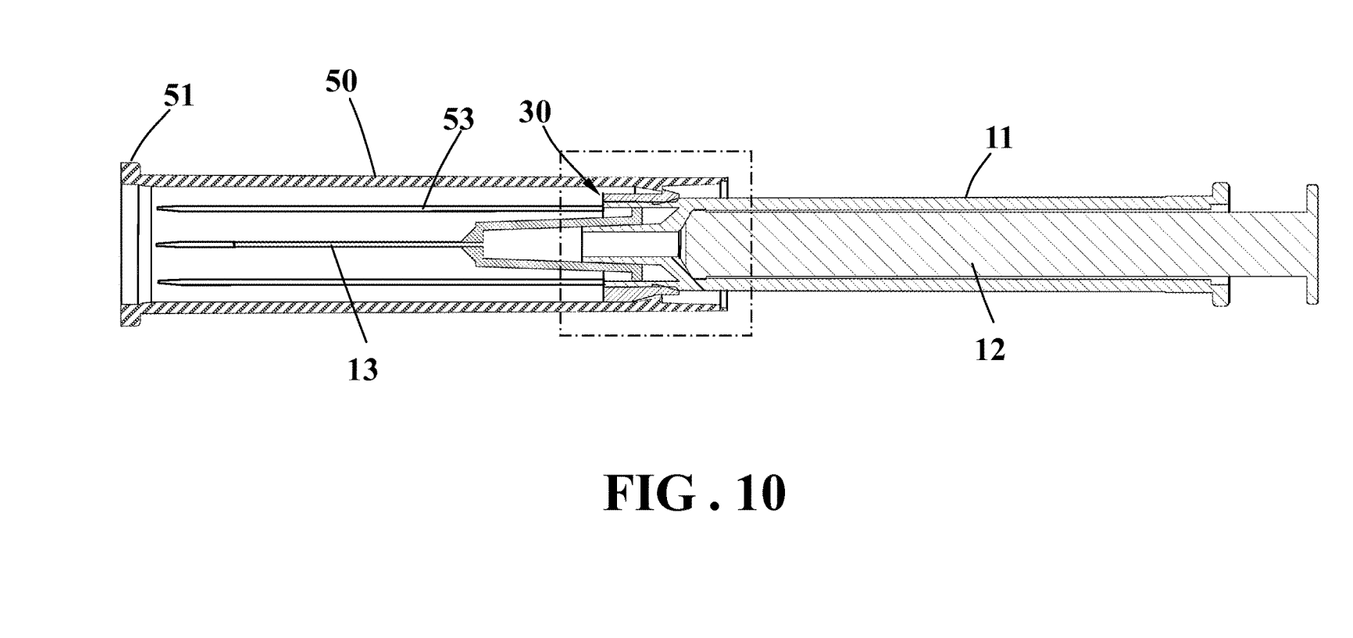
FIG. 10 is a cross-sectional view of the syringe assembly in another position than shown in FIG. 9.
Figure 12:
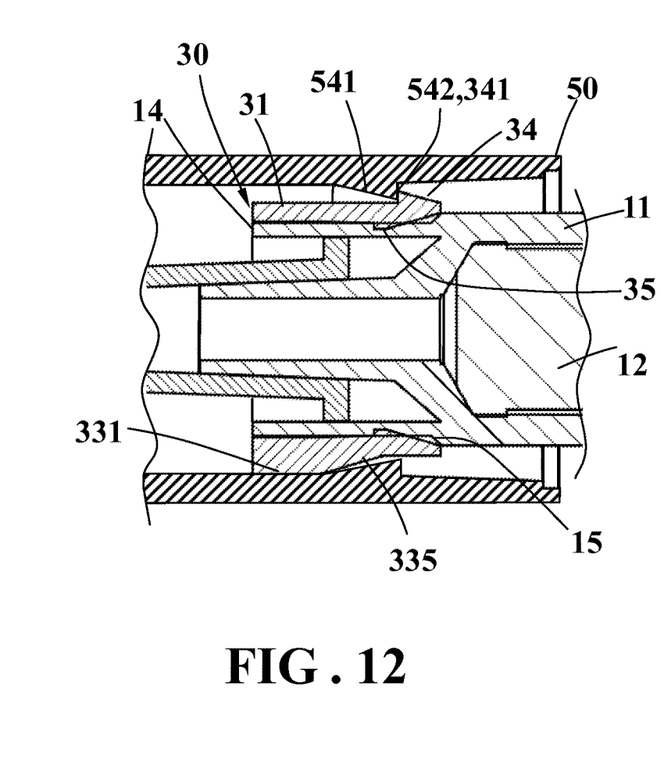
FIG. 12 is an enlarged partial view of the syringe assembly shown in FIG. 10.

Referring to FIGS. 8, 10 and 12, the protective sleeve 50 includes an annular rib 54 formed on the internal side, near the rear end. The annular rib 54 includes a slope 541 and a shoulder 542. The highest point of the slope 541 is connected to the shoulder 542, which faces the rear end of the protective sleeve 50. After the syringe 10 is used, the needle 13 must be covered so that the needle 13 cannot hurt a medical person. To this end, a force is exerted on the protective sleeve 50 to move the protective sleeve 50 toward the needle 13. The movement of the protective sleeve 50 experiences resistance in the beginning because the slopes 335 of the first group of teeth 33 of the locking element 30 abut against the frusto-conical face 52 of the protective sleeve 50 and the longitudinal ribs 53. Once the force exceeds the resistance, the frusto-conical face 52 of the protective sleeve 50 and longitudinal ribs 53 can be moved past the slopes 335 of the first group of teeth 33 of the locking, element 30 since the plastic material of the protective sleeve 50 is slightly elastic. Thus, the protective sleeve 50 can be moved toward the needle 13. During the movement of the protective sleeve 50, friction occurs as the longitudinal ribs 53 are moved past the crowns 331 of the first group of teeth 33. Hence, the movement of the protective sleeve 50 is contained and does not get excessively fast. The annular flange 51 is used for contact with a user's finger to avoid slipping of the finger on the protective sleeve 50.

The slope 541 of the annular rib 54 formed at the rear end of the internal side of the protective sleeve 50 has already been moved past the second group of teeth 34 of the locking element 30 by the time when the protective sleeve 50 completely covers the needle 13. The slopes 335 of the first group of teeth 33 of the locking element 30 are in contact with the slope 541 of the annular rib 54 of the protective sleeve 50 to cause intensive resistance against further forward movement of the protective sleeve 50, i.e., the protective sleeve 50 cannot be moved past the first group of teeth 33. The first ends 341 of the teeth 34 abut against the shoulder 542 of the annular rib 54 so that the protective sleeve 50 cannot be moved backwards. Thus, the locking element 30 keeps the protective sleeve 50 in position, i.e., the locking element 30 keeps the protective sleeve 50 covering the needle 13.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined, in the claims.

The invention claimed is:

1. A syringe assembly comprising:
   a syringe 10 comprising:
      a cylinder 11 formed with a front end 14;
      a plunger 12 movably inserted in the cylinder 11; and
      a needle 13 connected to the front end 14 of the cylinder 11;
   a locking element 30 comprising:
      an annular body 31 located on and around the front end 14 of the cylinder 11 and formed with an external side and an internal side;

a first group of teeth 33 evenly formed on the external side of the annular body 31 near a front end and separated by a first group of gaps 32, wherein each of the teeth 33 in the first group comprises a crown 331 and a slope 335 formed next to the crown 331; and a second group of teeth 34 evenly formed on the external side of the annular body 31 near a rear end and separated by a second group of gaps 37 aligned to the first group of teeth 33, wherein each of the teeth 34 in the second group is made with a thickness that gets smaller in a direction from a front end toward a rear end; and a protective sleeve 50 being movable along the cylinder 11 between a first position and a second position, and comprising:

an internal side;

an annular rib 54 formed on the internal side of the protective sleeve 50 near a rear end and with a slope 541 and a shoulder 542 connected to a highest point of the slope 541 such that the shoulder 542 faces the rear end of the protective sleeve 50; and a frusto-conical face 52 formed on the internal side of the protective sleeve 50 near a front end;

wherein the protective sleeve 50 only covers the cylinder 11 in the first position, and the slopes 335 of the first group of teeth 33 of the locking element 30 abut against the frusto-conical face 52 of the protective sleeve 50 to keep the protective sleeve 50 in the first position; and wherein the protective sleeve 50 covers the needle 13 in the second position, and the second group of teeth 34 of the locking element 30 abuts against the shoulder 542 of the annular rib 54 of the protective sleeve 50 while the slopes 335 of the first group of teeth 33 of the locking element 30 abut against the slope 541 of the annular rib 54 of the protective sleeve 50, thus keeping the protective sleeve 50 in the second position.

2. The syringe assembly according to claim 1, wherein the locking element 30 further comprises a third group of teeth 35 evenly formed on an internal side near the second group of teeth 34, wherein the third group of teeth 35 is adapted for abutment against the front end 14 of the cylinder 11 to position the locking element 30 on and around the front end 14 of the cylinder 11.

3. The syringe assembly according to claim 2, wherein each of the teeth 35 in the third group comprises a crown 351 and a slope 355 extending from the crown 351 thereof, wherein the slope 355 of each of the teeth 35 in the third group comprises a highest point connected to the crown of the same and a lowest point connected to the internal side of the annular body 31.

4. The syringe assembly according to claim 2, wherein the annular body 31 comprises a frusto-conical face 36 on the internal side near the third group of teeth 35, and the frusto-conical face 36 comprises a smallest portion connected to a lowest point of each of the teeth 35 in the third group.

5. The syringe assembly according to claim 1, wherein the front end 14 of the cylinder 11 is made with an external diameter smaller than that of an other portion of the cylinder 11, thus forming an annular shoulder 15 next to the front end 14 of the cylinder 11, wherein the locking element 30 is located on and around the front end 14 of the cylinder 11 and abuts against the annular shoulder 15.

6. The syringe assembly according to claim 1, wherein the protective sleeve 50 comprises an annular flange 51 formed on an external side.

7. The syringe assembly according to claim 1, wherein the protective sleeve 50 comprises longitudinal ribs 53 evenly formed on the internal side of the protective sleeve 50.

8. The syringe assembly according to claim 7, wherein each of the longitudinal ribs 53 comprises a front end connected to a largest portion of the frusto-conical face 52 of the protective sleeve 50.

* * * * *